United States Patent
Temple et al.

(10) Patent No.: US 10,645,921 B2
(45) Date of Patent: May 12, 2020

(54) VIABLE DISC REGENERATIVE COMPOSITION AND METHOD OF MANUFACTURE AND USE

(71) Applicant: Vivex Biologics Group, Inc., Atlanta, GA (US)

(72) Inventors: Harry Thomas Temple, Miami, FL (US); Timothy Ganey, Tampa, FL (US); Stephanie Gonzalez, Miami, FL (US); Tracy Scott Anderson, Atlanta, GA (US); Shabnam Namin, Miami, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 0 days.

(21) Appl. No.: 15/400,392

(22) Filed: Jan. 6, 2017

(65) Prior Publication Data
US 2018/0169301 A1    Jun. 21, 2018

Related U.S. Application Data

(60) Provisional application No. 62/436,681, filed on Dec. 20, 2016.

(51) Int. Cl.
*A01N 1/02* (2006.01)
*A61L 27/36* (2006.01)
*A61L 27/38* (2006.01)

(52) U.S. Cl.
CPC ......... *A01N 1/0284* (2013.01); *A01N 1/0221* (2013.01); *A01N 1/0231* (2013.01); *A61L 27/365* (2013.01); *A61L 27/3687* (2013.01); *A61L 27/3691* (2013.01); *A61L 27/3821* (2013.01); *A01N 1/0278* (2013.01); *A61L 2430/38* (2013.01)

(58) Field of Classification Search
CPC ............. A61L 27/3658; A61L 27/3683; A61L 27/3821; A61L 2430/38
See application file for complete search history.

(56) References Cited

U.S. PATENT DOCUMENTS

| | | | |
|---|---|---|---|
| 6,240,926 B1 | 6/2001 | Chin et al. | |
| 6,344,058 B1 | 2/2002 | Ferree | |
| 7,713,303 B2 | 5/2010 | Trieu et al. | |
| 8,227,246 B2 | 7/2012 | Kukekoev et al. | |
| 8,629,122 B2 | 1/2014 | Takahashi et al. | |
| 2003/0069639 A1 | 4/2003 | Sander et al. | |
| 2008/0014179 A1 | 1/2008 | Ferree | |
| 2013/0078222 A1 | 3/2013 | Sakai et al. | |
| 2014/0286912 A1 | 9/2014 | Ionescu et al. | |
| 2016/0338844 A1* | 11/2016 | Malinin | A61L 27/3608 |

OTHER PUBLICATIONS

Resonance. Datasheet [online] Merriam-Webster, 2017 [retrieved on Apr. 14, 2017]. Retrieved from the Internet: <URL: https://www.merriam-webster.com/dictionary/resonance>.*
Satience. Datasheet [online] Merriam-Webster, 2017 [retrieved on Apr. 14, 2017]. Retrieved from the Internet: <URL: https://www.merriam-webster.com/dictionary/satience>.*
Extant. Datasheet [online] Merriam-Webster, 2017 [retrieved on Apr. 14, 2017]. Retrieved from the Internet: <URL: https://www.merriam-webster.com/dictionary/extant>.*
Metabolome. Datasheet [online] Oxford English Dictionary, 2017 [retrieved on Apr. 14, 2017]. Retrieved from the Internet: <URL: https://en.oxforddictionaries.com/definition/metabolome>.*
Syringe Needle Gauge Chart. Datasheet [online]. Sigma-Aldrich, 2018 [retrieved on Oct. 16, 2018]. Retrieved from the Internet: <URL: https://www.sigmaaldrich.com/chemistry/stockroonn-reagents/learning-center/technical-library/needle-gauge-chart.html>. (Year: 2018).*
Matsumura et al., Polyampholytes as cryoprotective agents for mammalian cell cryopreservation. Cell Transplantation, vol. 19 (2010) pp. 691-699 (Year: 2010).*
Kucia et al., A population of very small embryonic-like (VSEL) CXCR4+SSEA-1+Oct-4+ stem cells identified in adult bone marrow. Leukemia, vol. 20 (2006) pp. 857-869. (Year: 2006).*

* cited by examiner

*Primary Examiner* — Kara D Johnson
(74) *Attorney, Agent, or Firm* — David L. King

(57) ABSTRACT

A viable disc regenerative composition has a micronized material of nucleus pulposus and a biological composition made from a mixture of mechanically selected allogeneic biologic material derived from bone marrow having non-whole cellular components including vesicular components and active and inactive components of biological activity, cell fragments, cellular excretions, cellular derivatives, and extracellular components; and wherein the mixture is compatible with biologic function and further includes non-expanded whole cells. The biological composition is predisposed to demonstrate or support elaboration of active volume or spatial geometry consistent in morphology with that of disc tissue. The viable disc regenerative composition extends regenerative resonance that compliments or mimics disc tissue complexity.

11 Claims, 18 Drawing Sheets
(18 of 18 Drawing Sheet(s) Filed in Color)

210  212  214  216

Percent recovery from freeze at 6 Months

VIABLE DISC REGENERATIVE COMPOSITION AND METHOD OF MANUFACTURE AND USE

TECHNICAL FIELD

The present invention relates to a spinal disc regenerative composition having micronized nucleus pulposus and marrow isolated multilineage-inducible (MIAMI) cells and method of manufacture and use.

BACKGROUND OF THE INVENTION

Intervertebral discs are soft and compressible. They are interposed between adjacent vertebral body elements of the spine. They act as shock absorbers for the spine, allowing it to flex, bend, and rotate. Degenerative disc disease can occur throughout the spine, but most often occurs in the discs in the lower back (lumbar region) and the neck (cervical region).

As the process of degeneration continues, micro tears or cracks occur in the outer layer (annulus fibrosus) of the disc. The jellylike material inside the disc (nucleus pulposus) may be forced out through the tears or cracks in the annulus, which causes the disc to bulge, break open (rupture), or break into fragments.

The economic impact of degenerative disc disease is enormous accounting for a significant morbidity and lost wages.

The physical properties of the disc are the nucleus pulposus which is composed of type II collagen and the annulus fibrosis which surrounds the disc and gives it significant form. The annulus composed of type I collagen. The nucleus pulposus is largely made up of molecules called proteoglycans. These proteoglycans have an affinity for water. It is this retention of water and the stoichiometry of folded molecules that is responsible for the unique mechanical properties of the disc. If these proteoglycans are depleted, the discs become more rigid and the loss of fluid results in a disc that is thinner and less compliant. Clinically this results in narrowing of the distances between the vertebral elements. This is best seen on magnetic resonance imaging. Typically discs have a bright signal on T2 pulse-weighted sequences and they are hypointense on corresponding T1 images. This is due to the high fluid content of the discs. As the disc loses fluid i.e. the loss of proteoglycans, the disc loses its water signal and becomes anhidrotic and eventually mineralizes. As a result, these individuals develop the symptoms in the spine contributable to loss of the normal disc architecture. As the process of degeneration continues, one develops micro tears or cracks and fissures in the annulus fibrosis and through these cracks and fissures the nucleus pulposus, which is largely gelatinous, may extrude. The extruded disc material may efface the dura and cause significant nerve compression which may result in traumatic neuritic pain and or motor loss. Therefore, once these early changes in disc degeneration are recognized, it may be prudent to replenish the disc with proteoglycans. Currently, synthetic and artificial substitutes are used to stimulate repair.

SUMMARY OF THE INVENTION

A viable disc regenerative composition has a micronized material of nucleus pulposus and a biological composition made from a mixture of mechanically selected allogeneic biologic material derived from bone marrow having non-whole cellular components including vesicular components and active and inactive components of biological activity, cell fragments, cellular excretions, cellular derivatives, and extracellular components; and wherein the mixture is compatible with biologic function and further includes non-expanded whole cells. The biological composition is predisposed to demonstrate or support elaboration of active volume or spatial geometry consistent in morphology with that of disc tissue. The viable disc regenerative composition extends regenerative resonance that compliments or mimics disc tissue complexity.

The present invention provides a novel way to replenish the disc. These novel disc compositions may be used to repair degenerative discs. There is no better source of proteoglycans than the actual disc material itself. To this end, a technique has been developed to remove the nucleus pulposus and retool the morphology of the nucleus pulposus to create a powder material that is dry and can be stored at room temperature for long periods of time. This powder can then be reconstituted with a variety of fluids, the most suitable being normal saline or lactated ringers solution to form a flowable mixture.

The powder is mixed with a biological composition preferably having stem cells that are derived from bone marrow. In addition, it could also be combined with micronized amnion, platelet-rich plasma, and a variety of growth factors that can be encapsulated into pharmacologically active microspheres otherwise known as PAMS. The powder could also be combined with genetically altered cells that produce large amounts of glycosaminoglycans, collagen Type 1 or glucose to form the flowable mixture. The micronized material when rehydrated has a high viscosity and allows the rehydrated material to be flowable as injectable through a cannula. This allows the rehydrated material to be stored in a syringe or other injectable device for insertion into a damaged disc to be treated.

This flowable mixture forms a composite composition between the micronized nucleus pulposus that can then be injected using a syringe or any suitable injection delivery device through a very small cannula as small as 2 mm into the disc space. This instrument can be inserted percutaneously into the disc itself during the process of discography. The flowable material of this composite composition is of a sufficiently high viscosity that once hydrated will not necessarily leak out through the injection portal or through pre-existing cracks and fissures in the annulus fibrosus. If, however, these cracks and fissures are substantial, they could be sealed with fibrin glue as part of the procedure of introducing the composites.

A biological composition that has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture is compatible with biologic function.

The mixture of mechanically selected material derived from bone marrow further preferably has non-expanded whole cells.

The combination of non-whole cell components with a select number of the non-expanded cells sustains pluripotency in the cells. The select number of the non-expanded cells includes differentiated committed cells and non-differentiated and non-committed cells.

In a preferred embodiment, the viable disc regenerative composition is predisposed to demonstrate or support elaboration of active volume or spatial geometry consistent in morphology with that of endogenous nucleus pulposus. The viable disc regenerative composition extends regenerative resonance that compliments or mimics the disc tissue complexity. The mixture is treated in a protectant or cryoprotectant prior to preservation or cryopreservation. The protectant or cryoprotectant creates a physical or electrical or chemical gradient or combination thereof for disc tissue regeneration. The gradient can have a physical characteristic of modulus or topography. The gradient can have a chemical characteristic of spatially changing compositions of density or species of functional molecules. Also, the gradient can have an electrical characteristic of charge based or pH based or electron affinities that confer metastability in biologic potential.

The bone marrow mixture which is derived from a cadaver has separation-enhanced cell vitality including one or more of the following: separating the cells heightens their vitality, reversing "arrest" of donors, responsive molecular coupling, matrix quest in neutralizing inflammation or satience by balancing stimulus for repair. The protectant or cryoprotectant is a polyampholyte. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C.

The viable disc regenerative composition's non-whole cellular component also can include organelle fragments and the active and inactive components of biological activity which can also include extants of the human metabolome.

A method of making a viable disc regenerative composition of the present invention has the steps of: collecting, recovering and processing bone marrow from a cadaver donor; mechanically separating the cellular or non-cellular components or a combination thereof of bone marrow from cadaverous bone; concentrating by centrifugation and filtering; separation by density gradient centrifugation; collecting cellular or non-cellular components or a combination thereof of predetermined density; washing the cellular or non-cellular components or a combination thereof to create the mixture; quantifying cell concentration not to exclude zero; suspending to a predetermined concentration in a polyampholyte cryoprotectant; freezing the mixture at a predetermined controlled rate; and packaging the mixture and separately packaged dehydrated micronized nucleus pulposus having particles in the size range of less than 300 μm separate. These particle size ranges can vary higher or lower depending on the application. At the time of use, the mixture is thawed by immersion in a warm water bath for 2-3 minutes at 37 degrees C. It is diluted in saline without spinning; and then the diluted mixture, with the nucleus pulposus being intermixed, can be implanted by packing, injection, scaffolding or any other suitable means into a disc to be repaired of a patient.

Definitions

As used herein and in the claims:

"Cryomill"—The CryoMill is tailored for cryogenic grinding. The grinding jar is continually cooled with liquid nitrogen from the integrated cooling system before and during the grinding process. Thus the sample is embrittled and the chemical composition is preserved. The liquid nitrogen circulates through the system and is continually replenished from an Autofill system in the exact amount which is required to keep the temperature at −196° C. Powerful impact ball milling results in a perfect grinding efficiency. The Autofill system avoids direct contact with LN2 and makes the operation very safe. Its versatility (cryogenic, wet and dry grinding at room temperature) makes the CryoMill the ideal grinder for quantities up to 20 ml. The grinding jar of the CryoMill performs radial oscillations in a horizontal position. The inertia of the grinding balls causes them to impact with high energy on the sample material at the rounded ends of the grinding jar and pulverize it. The grinding jar is continually cooled with liquid nitrogen from the integrated cooling system before and during the grinding process.

"Disc Desiccation"—Disc desiccation is an extremely common degenerative change of intervertebral discs. The incidence climbs with age, and to a large degree a gradual desiccation is a 'normal' part of disc aging. It results from replacement of the hydrophilic glycosaminoglycans within the nucleus pulposus with fibrocartilage.

"Freeze Drying"—Freeze-drying, also known as lyophilisation, lyophilization, or cryodesiccation, is a dehydration process typically used to preserve a perishable material or make the material more convenient for transport and stable at room temperatures in an appropriate contained or package. Freeze-drying works by freezing the material and then reducing the surrounding pressure to allow the frozen water in the material to sublimate directly from the solid phase to the gas phase.

"Hypothermic Dehydration"—hypothermic dehydration depends on placing the object at reduced temperatures above freezing point into a high vacuum chamber allowing it to dry to a desired residual moisture level. The result is dried tissue without fissures, microscopic ice crystal distortion and collapse phenomenon.

"Nucleus Pulposus"—Nucleus pulposus is the gel-like substance in the middle of the spinal disc. It is the remnant of the notochord. It functions to distribute hydraulic pressure in all directions within each disc under compressive loads. The nucleus pulposus consists of large vacuolated notochord cells, small chondrocyte-like cells, collagen fibrils, and proteoglycan aggrecans that aggregate through hyaluronic chains. Attached to each aggrecan molecule are the glycosaminoglycan (GAG) chains of chondroitin sulfate and keratan sulfate. Aggrecan is negatively charged, allowing the nucleus pulposus to attract water molecules. The amount of water and glycosaminoglycans decreases with age and degeneration.

"Proteoglycans"—Proteoglycans are proteins that are heavily glycosylated. The basic proteoglycan unit consists of a "core protein" with one or more covalently attached glycosaminoglycan (GAG) chain(s). The point of attachment is a Ser residue to which the glycosaminoglycan is joined through a tetrasaccharide bridge (e.g. chondroitin sulfate-GlcA-Gal-Gal-Xyl-PROTEIN). The Ser residue is generally in the sequence—Ser-Gly-X-Gly—(where X can be any amino acid residue, but Proline), although not every protein with this sequence has an attached glycosaminoglycan. The chains are long, linear carbohydrate polymers that are negatively charged under physiological conditions, due to the occurrence of sulfate and uronic acid groups. Proteoglycans occur in the connective tissue. Proteoglycans are a major component of the animal extracellular matrix, the "filler" substance existing between cells in an organism. Here they form large complexes, both to other proteoglycans, to hyaluronan and to fibrous matrix proteins (such as collagen). They are also involved in binding cations (such as sodium, potassium and calcium) and water, and also regulating the movement of molecules through the matrix. Evidence also shows they can affect the activity and stability of proteins and signaling molecules within the matrix. Individual functions of proteoglycans can be attributed to either the protein core or the attached GAG chain and serve as lubricants.

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

DPBS—Dulbecco's Phosphate Buffered Saline.

CBT-MIXER—Mixing blade for Cancellous Bone Tumbler Jar.

Cold Media—Media used during the preparation of vertebral bodies for initial processing.

Cryopreserved—Tissue frozen with the addition of, or in a solution containing, a cryoprotectant agent such as glycerol or dimethylsulfoxide.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee. The invention will be described by way of example and with reference to the accompanying drawings in which.

DETAILED DESCRIPTION OF THE INVENTION

With reference to the present invention FIGS. 1-4 are directed to the micronized nucleus pulposus component. FIGS. 5-15 are directed to the biological composition with stem cells and the combination of these provided as a packaged kit for use in disc repair. Charts 16-27 are directed to the manufacturing process.

Figure 1A:
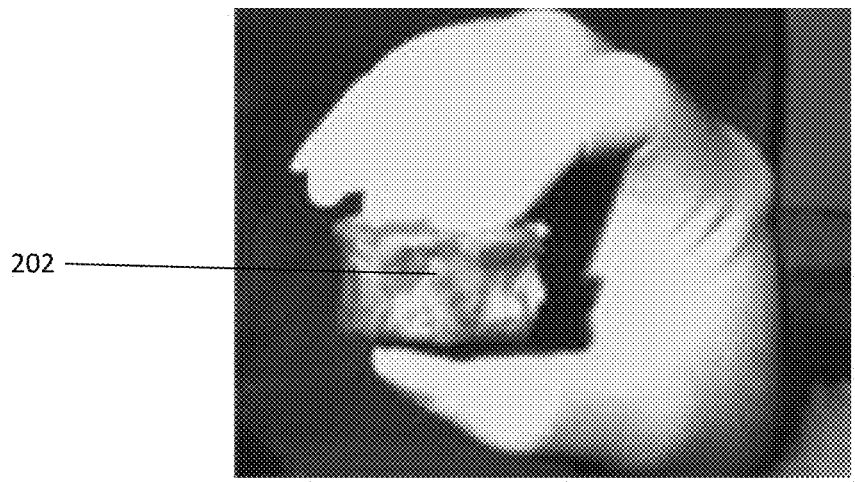
FIG. 1A is a photo of a spinal segment after being cut from a spine segment from which nucleus pulposus is extracted.
Figure 1B:
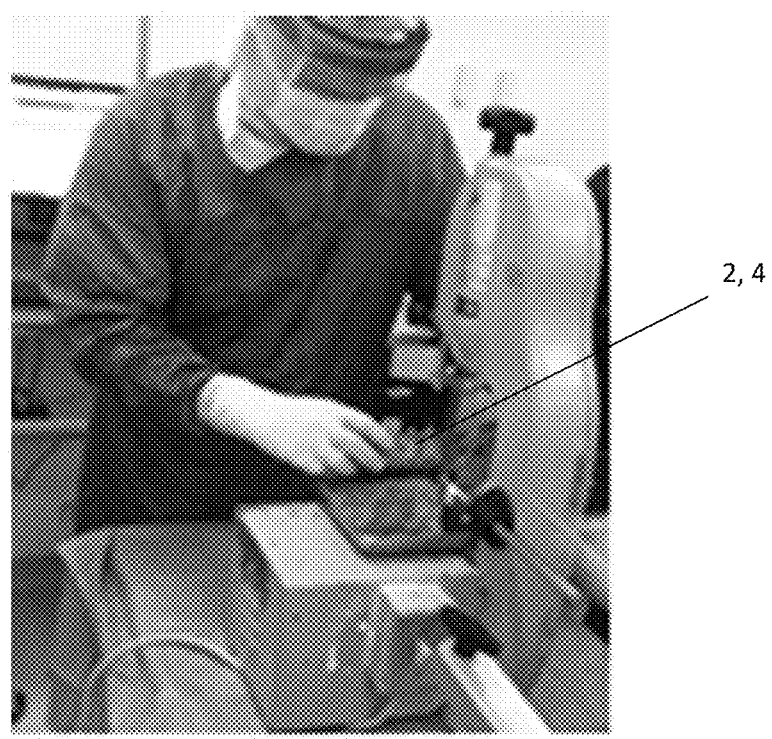
FIG. 1B is a photo of a vertebral spine segment wherein the adjacent vertebrae are cut, separated and the disc material removed.
Figure 2:
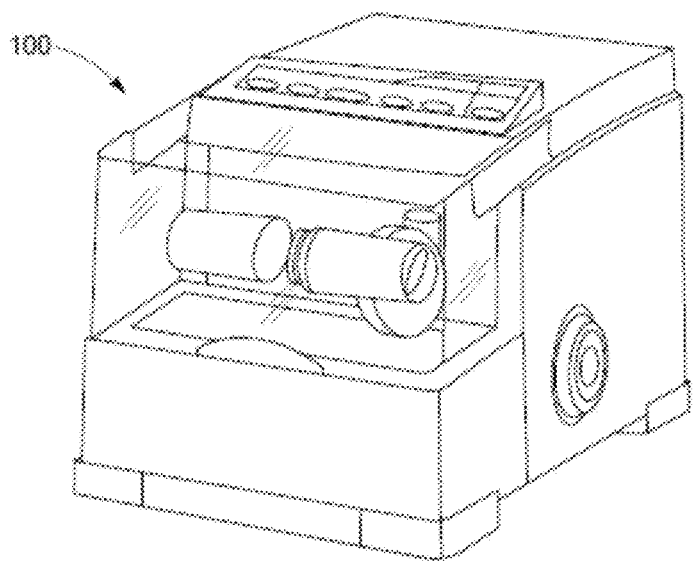
FIG. 2 is a photo of an exemplary cryomill.
Figure 3:
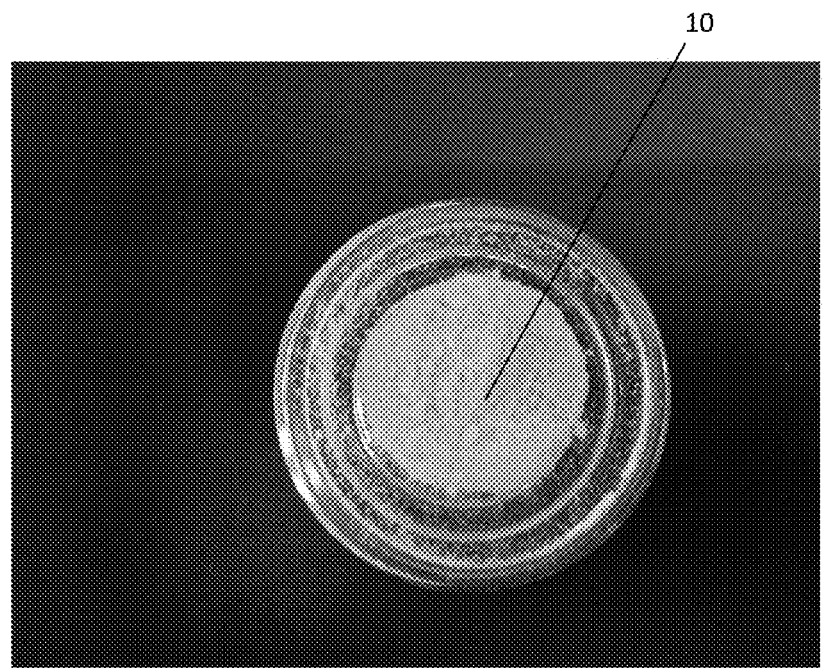
FIG. 3 is a photo of freeze dried disc material micronized to a fine powder.
Figure 4:
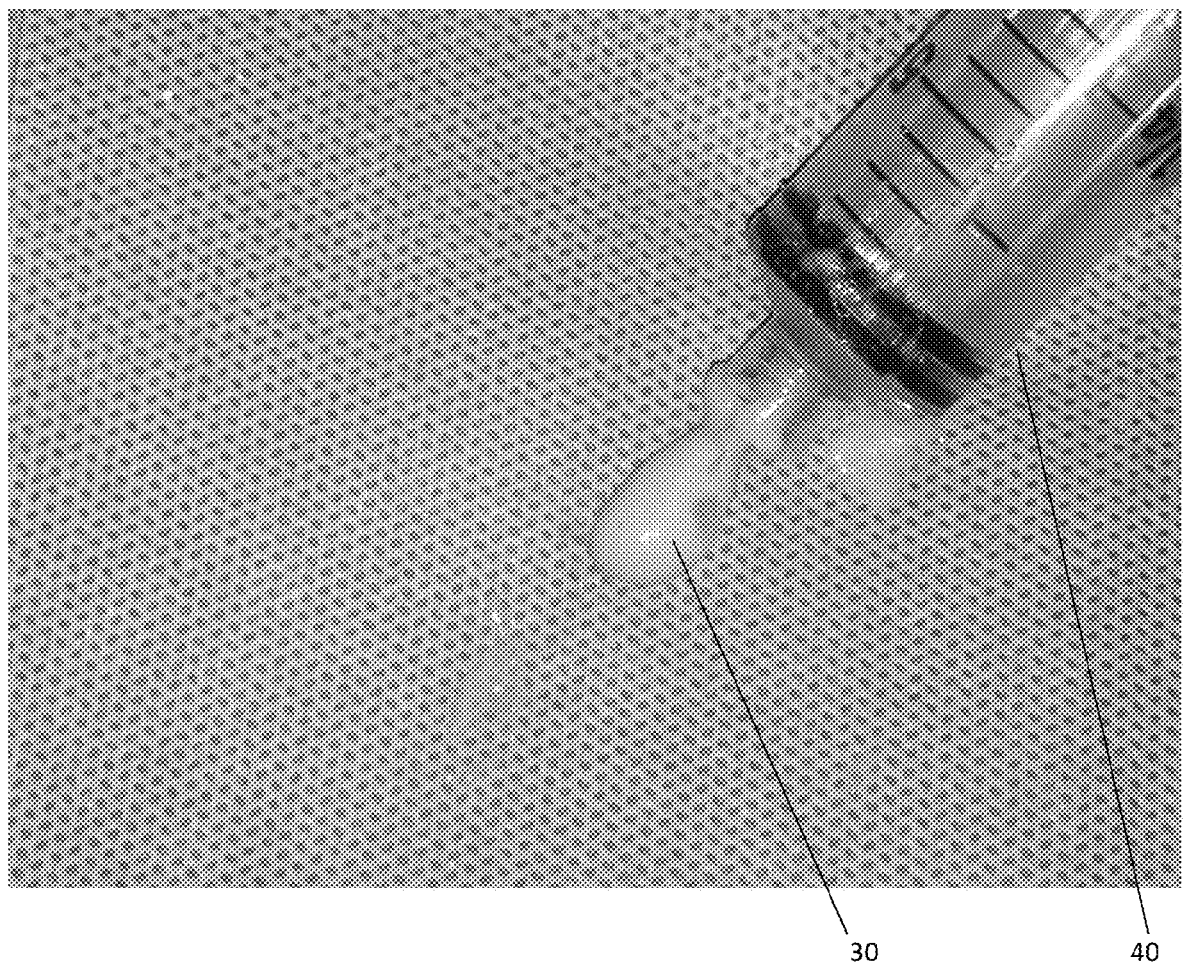
FIG. 4 is a photo showing the rehydrated disc material flowing from a syringe.

The actual disc material 6 is a recovered aseptically, preferably, from human cadaver spine segments 2 from approximately T9 to L5 as shown in FIG. 1A. These are done under sterile conditions. The spinal segments are immediately transferred to a processing room where the disc is isolated by cutting the junction between the end plate and the cancellous bone maintaining intact endplates of the vertebral body 4 above and below so as not to cause extrusion of the disc material as shown in FIG. 1B. The endplates are then removed and the nucleus pulposus is extracted using sharp dissection. The nucleus pulposus is then aggregated from all of the intervertebral discs for that particular case and are placed in a freeze drier and or cold desiccator where the moisture is removed to under 5 percent. The freeze dried material is then placed in aggregate into a cryomill 100, shown in FIG. 2, and micronized into a very fine powder 10 as shown in FIG. 3. Preferably, the mill 100 pulverizes the freeze dried nucleus pulposus at low temperatures not exceeding 40° C. to prevent material degradation. The micronized material has particles sized less than 400 microns preferably less than 300 microns. This fine powder 10, as shown in FIGS. 3 and 4, is then placed into a sterile container and can be stored under vacuum seal for long periods of time at room air. Once the fine powder material 10 is selected for administration, it is rehydrated using either normal saline, lactated ringers solution, blood, platelet rich plasma, or a combination of the above and mixed with the isolated stem cells. It is then injected into the disc space using a 2-4 mm cannula, the smaller the cannula the better to prevent extrusion of the material out of the disc space following administration. Any pre-existing cracks or fissures are then sealed with fibrin glue after administration of the composite material.

The inventor has developed a biochamber whereby a human disc can be placed in a physiologic environment and loaded biomechanically. Simultaneously, various parameters can be continuously measured such as cellular activity, oxygen tension and glucose depletion.

It is believed a degenerative disc can be recovered and placed in a biological incubator and injected with the rehydrated freeze dried nucleus pulposus powder and incubated over a period of time to demonstrate physiologic repair and healing of the disc by increased metabolic activity, water retention and improved biomechanical strength.

This exemplary test protocol can be used to confirm the efficacy of the various reconstituted rehydrated mixtures proposed herein.

This allows for a unique method of preparing the material composition of proteoglycan containing nucleus pulposus comprising the steps of: Aseptic recovery of cadaveric spine segments 2, 4 from T9 to L5 (FIGS. 1A and 1B); Removal of the discs 6 by cutting between the cancellous bone and vertebral endplate junction; Removing the normal nucleus pulposus; Freeze drying the nucleus pulposus from multiple disc segments; Placing the freeze dried material into a cryomill 100 (FIG. 2); Placing the micronized disc material 10 into a sterile container for later use (FIG. 3).

Additionally, a test procedure may be used to confirm viability of the material which includes the step of: mixing the micronized disc material 10 with saline, stem cells, micronized amnion, platelet rich plasma, growth factors, PAMS (pharmacologically active microspheres), genetically altered cells that produce glycosaminoglycans. This rehydrated mixture 30 can be made a flowable material suitable for delivery from a nozzle type container such as a syringe 40, shown in FIG. 4. Once this micronized powder 10 is rehydrated it can be delivered to treat damaged or degenerative disc repair.

The treatment method can include the steps of: injecting the matrix composite through a 2-4 mm cannula into the disc space. Smaller apertures through which this material may be injected may be preferable to limit extrusion of the material out of the disc space.

The spinal disc tissue can be prepared by dehydration at hypothermic temperatures.

With general reference to FIGS. 5-15 which show how a regenerative biological composition 201 is made from bone marrow 200, it is believed best understood by the methods used to process and recover the biological composition, as illustrated in the FIGS. 5-10.

Figure 5:
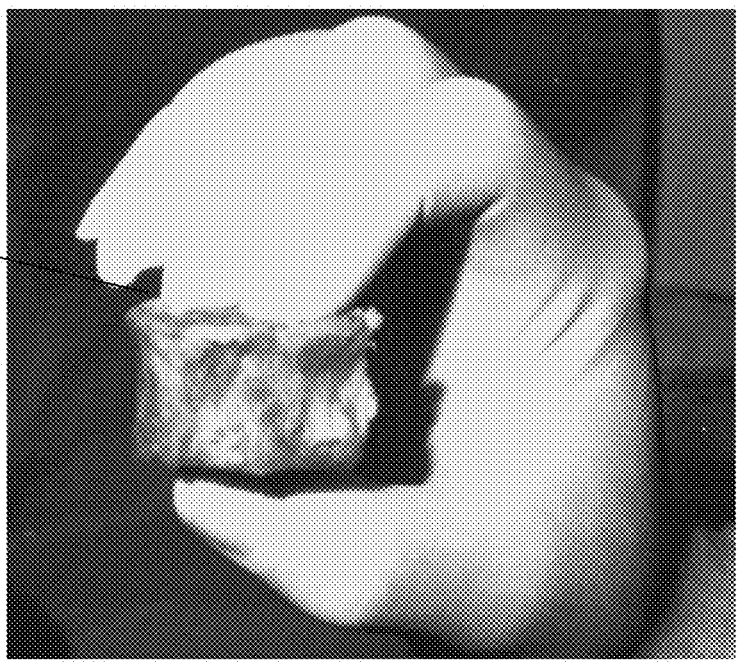
FIG. 5 shows a second photograph of a cut vertebral body taken from a spine of a cadaver donor from which stem cells are extracted.
Figure 6:
FIG. 6 shows a photograph of the vertebral body after being cut into cubic pieces and immersed in a packing media.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (lg/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 5.

Once a cleaned vertebral body 202 is obtained, the next step involves cutting each vertebral body 202 into pieces, each piece 204 roughly 1 cm3. The cut pieces 204 being immersed in a packing media 400. The exemplary packing media can be DMEM with 0.5 mlHeparin and 1.25 ml of DNAse added.

Figure 7:
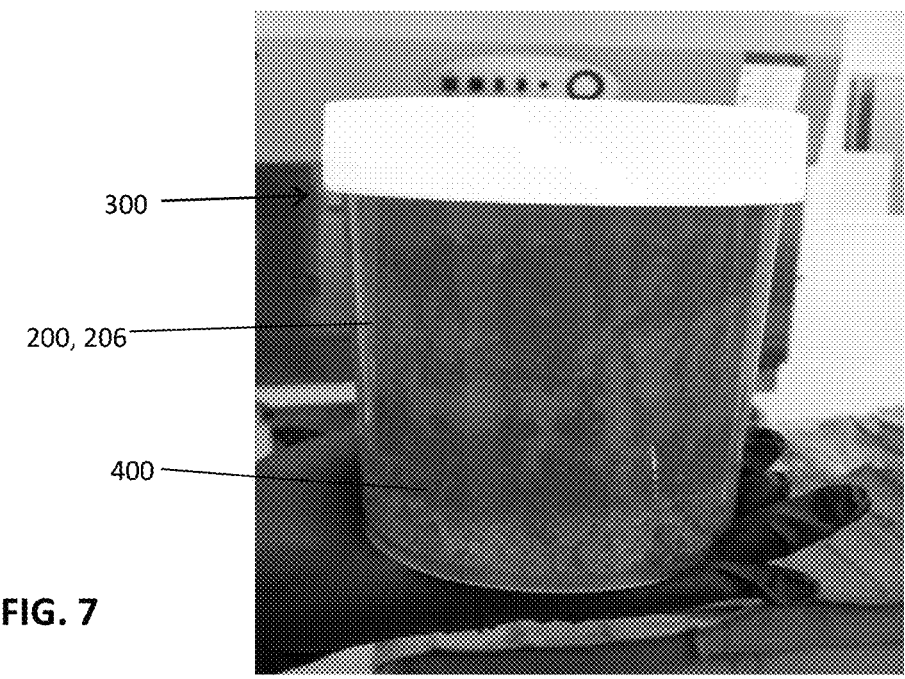
FIG. 7 shows a photograph of the bulk bone material after being ground and immersed in packing media and placed in a jar for later tumbling.
Figure 8:
FIG. 8 shows a photograph of the jar with a CBT-Mixer connected to a tumbler.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400, as illustrated in FIG. 7. At this point, the crushed bone 206, including cellular soft marrow 200, is intermixed.

Figure 9:
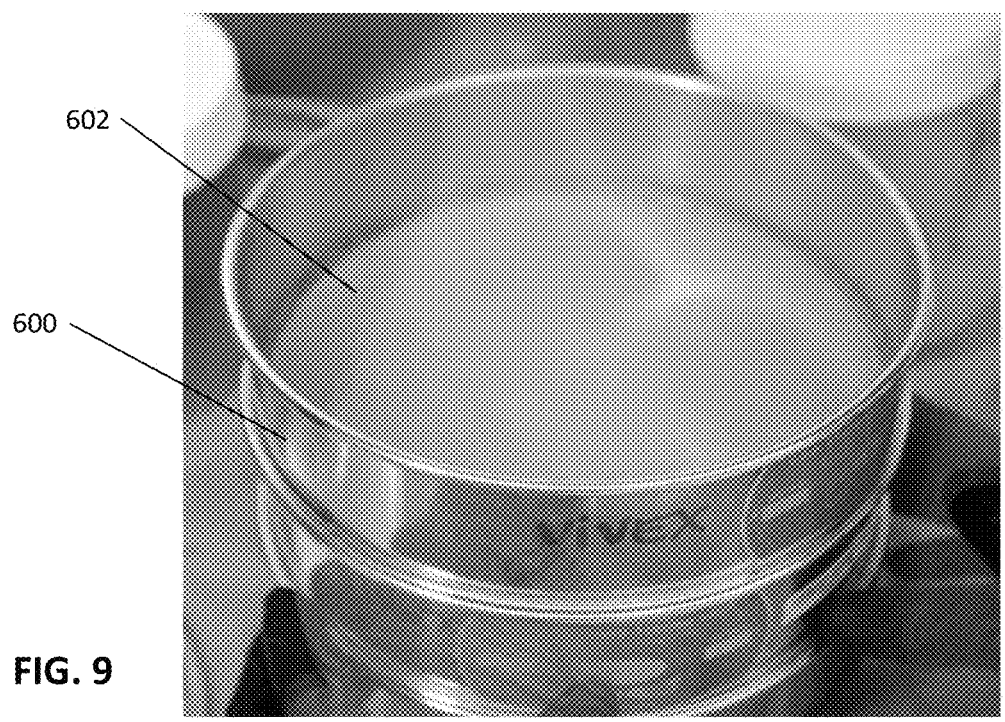
FIG. 9 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar 300 with a CBT-Mixer in the jar extending and connected 700 to the bone tumbler 500 shown in FIG. 8. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 μm and 180 μm, as shown in FIG. 9.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-μm and the bottom pan sieve. Discard decanted fluid. | Use the 500-μm 180-μm and bottom pan sieve. Collect decanted fluid. | Use the 500-μm 180-μm and bottom pan sieve. Collect decanted fluid. | Use the 500-μm 180-μm and bottom pan sieve. Collect decanted fluid. |

-continued

| Step | Cycle 1 | Cycle 2 | Cycle 3 | Cycle 4 |
|---|---|---|---|---|
| Centrifuge | N/A | Use decanted fluid. | Use decanted fluid. | Use decanted fluid. |

Figure 11:
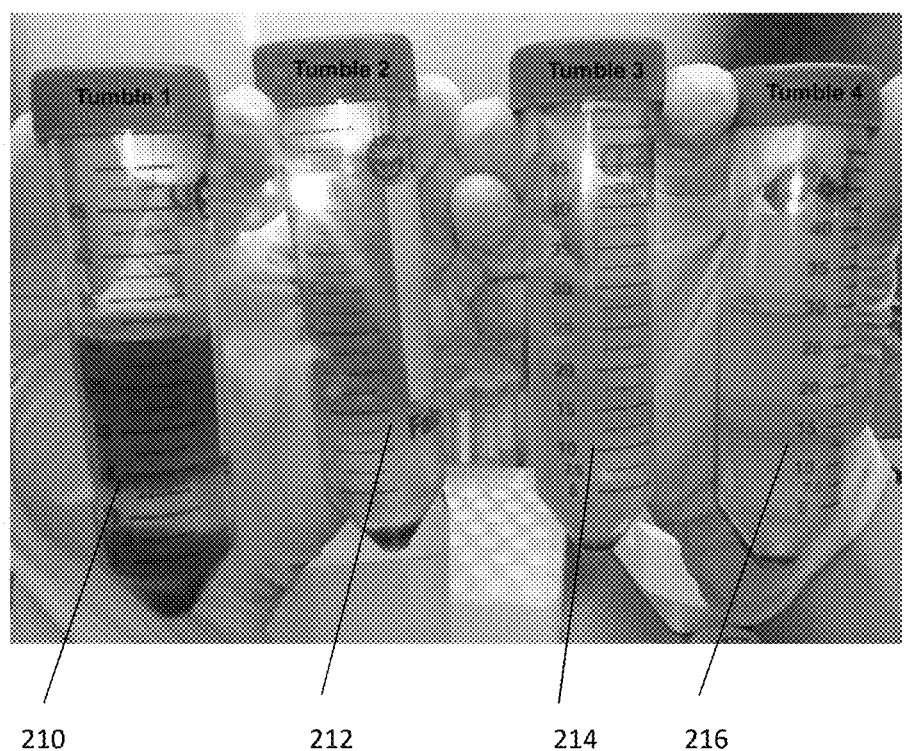
FIG. 11 is a photograph showing the four tumbling steps 1-4 by exemplary collection and Ficoll separation of the decanted fluids, the fluid in tumble 1 being completely discarded to remove unwanted debris.
Figure 12A:
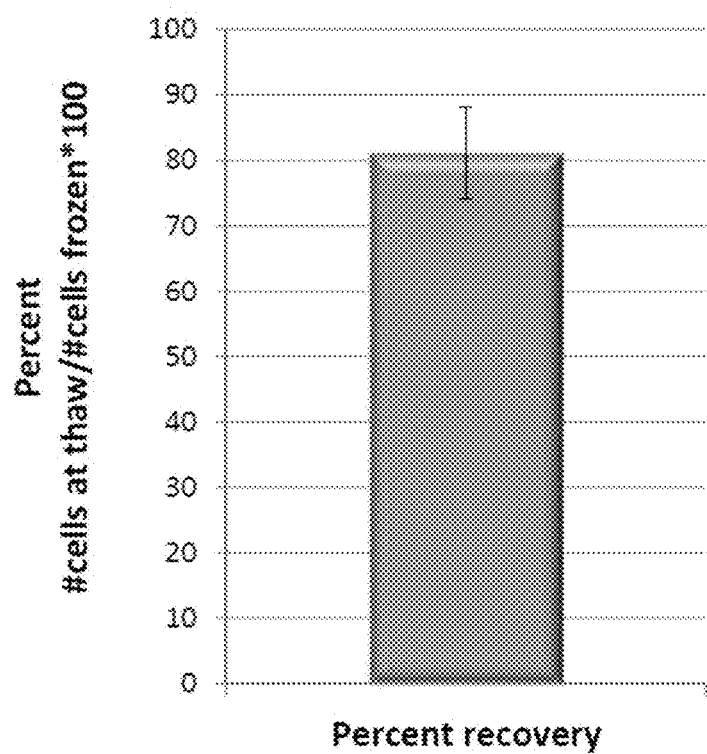
FIG. 12A is a chart showing the percent recovery at 6 months after cryofreezing the mixture of 1 ml at $1.1 \times 10^6$ cells and thawing.
Figure 12B:
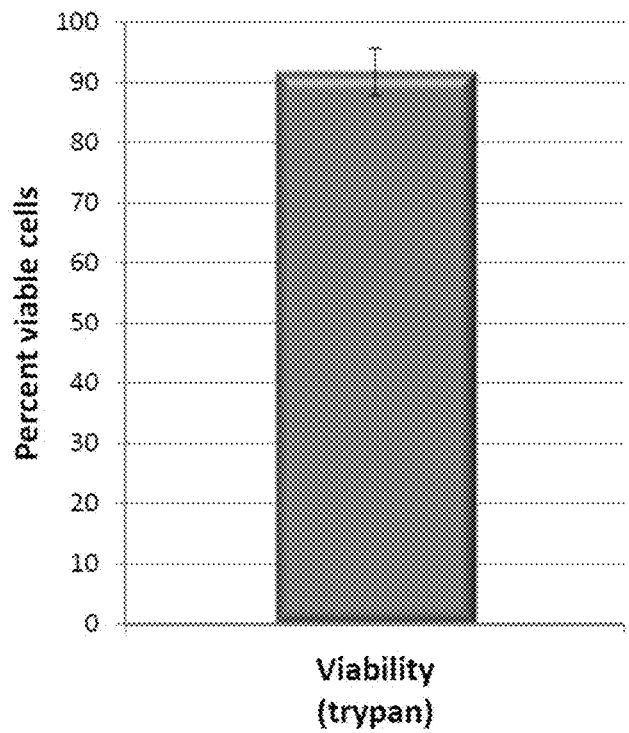
FIG. 12B is a chart showing the viability at 6 months after cryofreezing and thawing.
Figure 12C:
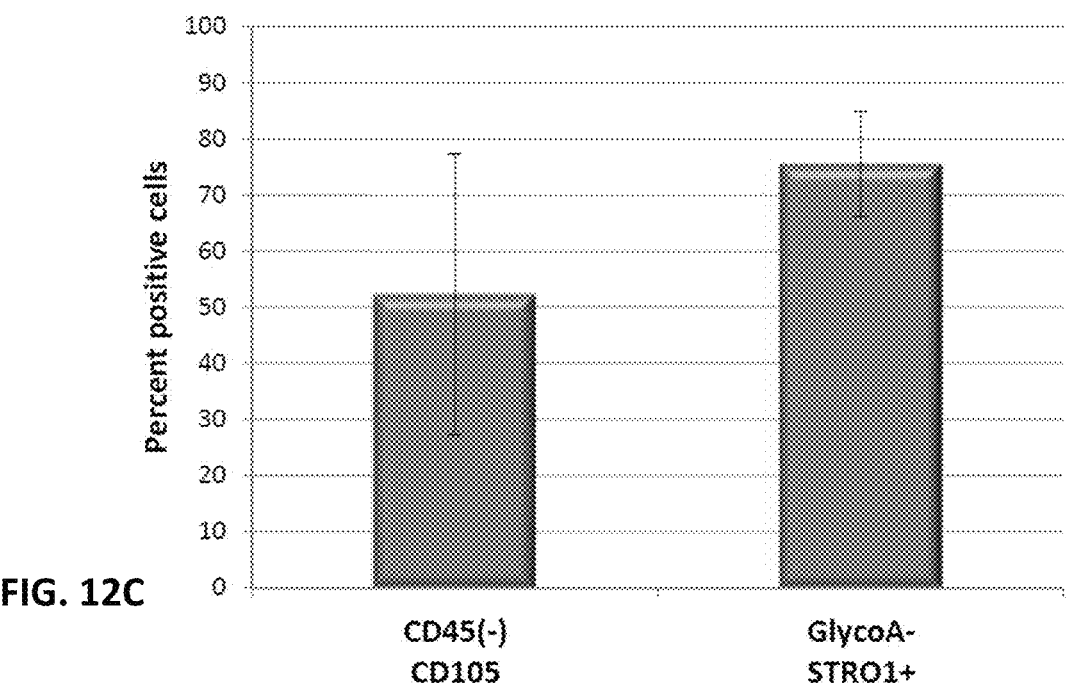
FIG. 12C shows a chart at 6 months of MSC markers by percentage of cells.

In cycle 1, the decanted fluid 210 is discarded. To best understand this, an exemplary FIG. 11 shows conical tubes 10 with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This FIG. 11 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid 220. Then the centrifugation of the combined decanted fluid 220 occurs by placing the fluid 220 in a number of 250 ml conical tubes using a 100 ml pipette. The centrifuge is programmed to 280×g for 10 minutes at room temperature, preferably about 20 degrees C. The fluid 220 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 10:
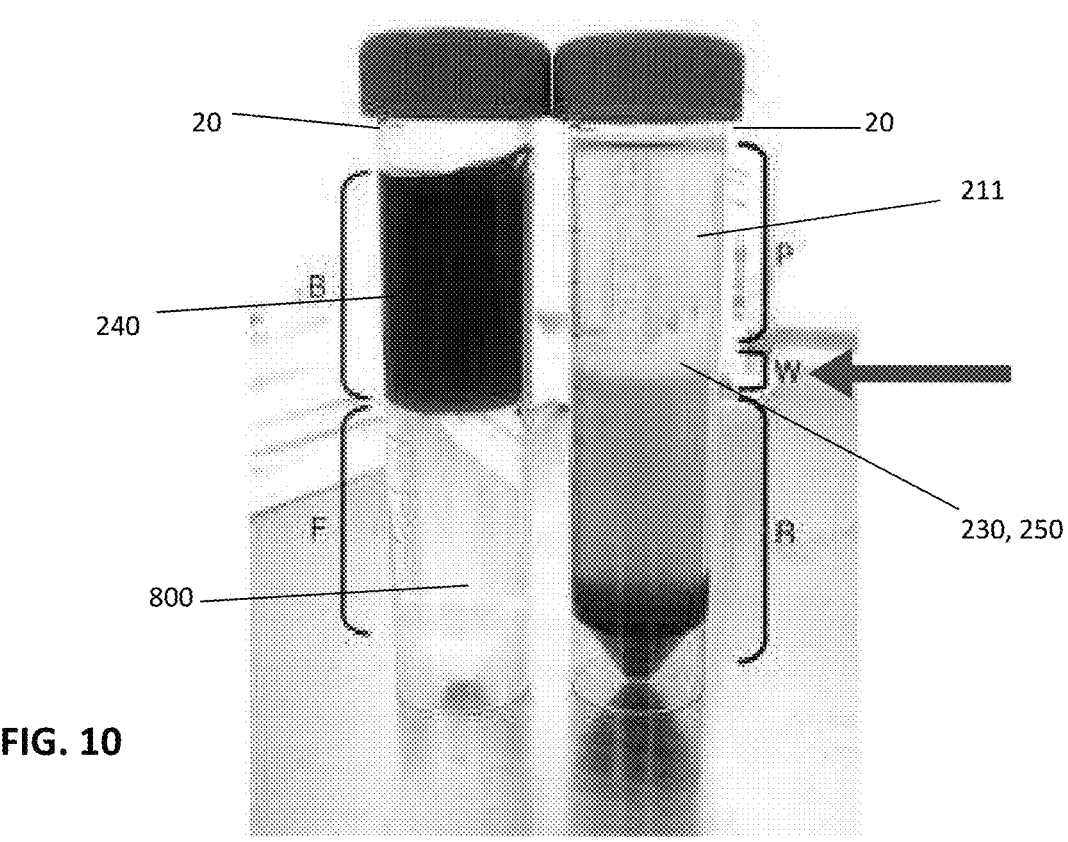
FIG. 10 shows a photograph of two 50 ml vials, the one on the left being prior to centrifuging with the Ficoll that is commercially available at the bottom and the material above it. The 50 ml vial on the right is after centrifuging showing the cell interface layer.

After this as shown in FIG. 10, the step of separating the cells 240 by a density centrifugation occurs. The mixture including whole cells 240 is placed in 50 ml conical tubes 20 with Ficoll 800 and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid 211 above the interface is removed and the interface 230 including the desired components which can include whole cells 250 is then collected using a 5 ml pipette and transferred into new 50 ml conical tubes ensuring no tube has more than 10 ml. Then the volume is brought to 50 ml by adding DPBS and centrifuged at 400×g for 5 minutes at room temperature, preferably about 20 degrees C. and the supernatant is removed leaving a pellet. Each 50 ml tube is then filled up to 50 ml with DPBS to resuspend the pellet. Another centrifugation occurs and the supernatant is removed and the remaining pellet is resuspended using the process media with no antibiotics. The suspension is then used to resuspend all the pellets in remaining tubes. The suspension volume is brought to 50 ml by adding processing media with no antibiotic. Then the suspension can be strained using a 100 μm cell strainer if any visual clumping is seen. These steps effectively wash the cells 250, if present, and the non-cellular components. A representative sample is then counted. The remaining, or a portion thereof, of the cellular or non-cellular components or a combination thereof is centrifuged and resuspended in the desired protectant after which it's placed in vials holding 1 ml.

In the preferred embodiment, this results in 1.1×106 cells per ml, but could cover any concentration from zero to less than 5.0×106 cells per ml depending on the desired concentration wanted per cc.

Once the cell count is established and each 1 ml suspension is established or quantified, the material is taken and suspended in a predetermined concentration of a polyampholyte cryoprotectant or any other suitable alternative protectant. When using the cryoprotectant, a freezing of the mixture at a predetermined control rate is required. Ideally, the application of a cryoprotectant coats each cell 250 and provides a protective coating to keep the cell viable during the freezing process. While the techniques for cryopreservation are well known, the present invention after being frozen has demonstrated remarkably unexpected results.

Figure 13A:
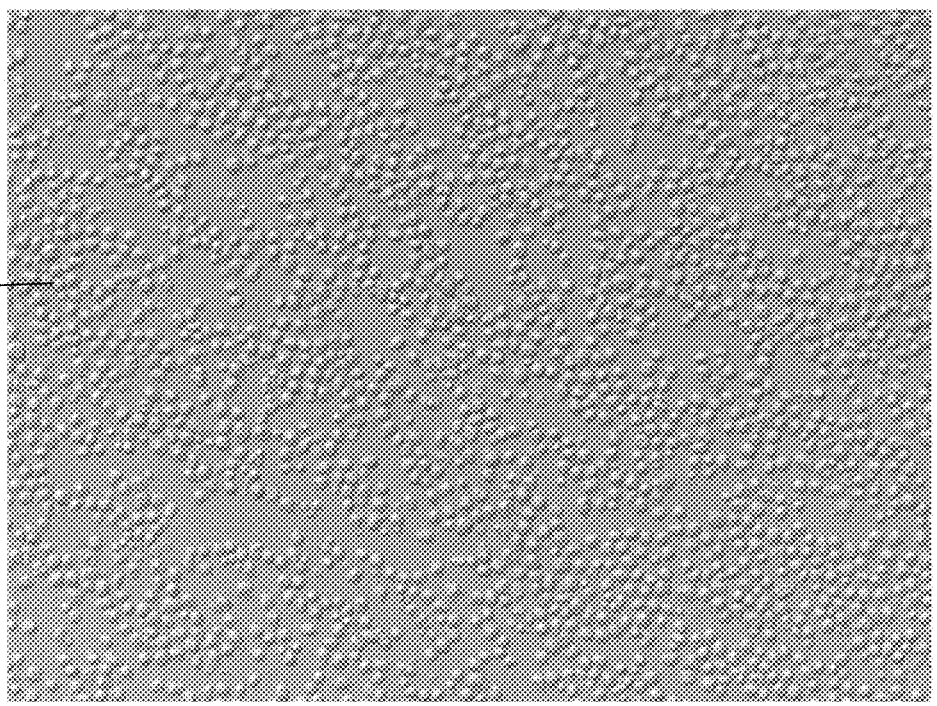
FIGS. 13A and 13B are photographs of cells thawed from a single sample and placed in media at 37 degrees C. overnight evidencing cell viability.
Figure 13B:
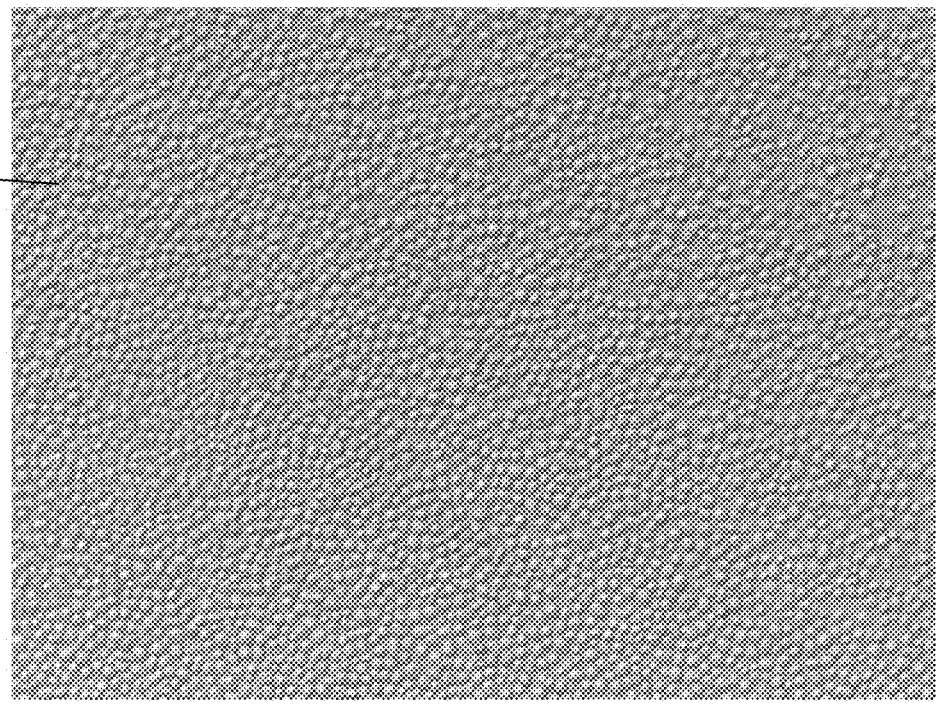
Figure 14:
FIG. 14 is a representative photograph of the final packaging.
Figure 15:
FIG. 15 is a photograph showing the micronized nucleus pulposus.

When thawed and a cell count is preformed after manufacture, the cell viability is 80 percent. Thawing is in a water bath warmed to 37 degrees C. for 2-3 minutes. After storage for 6 months, the cell viability is 91.0+/−3.8%. The percent recovery from freeze at 6 months thaw is 82.8+/−7.2%. The inventors have noted that the recovery count is lower than the viability to the lysis of undesirable GlycoA+ cells during freeze, a well-known occurrence. The unlysed desirable cells were viable at 91.0%. The inventors would also like to note that while thawed cells are generally suspended in FDS-supplemented media and spun, to better simulate how the product is actually used the cell recovery at six months was thawed and suspended in 3 ml of saline yielding a 4 ml suspension and that was not spun, but measured directly to simulate a real use injection. This allowed the cryopreservative to more effectively demonstrate that actual count of viable cells a patient would expect to receive and provides one explanation for this remarkable viability result. As shown in FIGS. 13A and 13B, the cells 250 are shown under magnification. In the cells at 6 months thaw the percent of positive cells for MSC markers, specifically CD105 and STRO1+ are 52 percent and 74 percent respectively, shown in FIGS. 12A-12C. These indicate the majority of cells are non-differentiated and directionally favorable for new bone formation.

When the mixture is prepared, it can have whole cells or even no whole cells, but will have the mechanically selected non-whole cellular components including vesicular components and active and inactive components of biological activity, cell fragments, cellular excretions, cellular derivatives, and extracellular components.

In the most preferred embodiment, the composition includes the whole cells in the mixture. In that embodiment, it is possible to provide nucleus pulposus particles with the mixture either in the mixture or separately to be combined at the time of use.

The overall manufacturing of the final product for transplant derived from human intervertebral discs is as outlined in the charts 16-27. The final Via Disc allograft is derived from qualified cadaveric donors and processed using aseptic product techniques in accordance with FDA (21 CFR Part 1271) and to the standards of the American Association of Tissue Banks (AATB). The intent of the final processed Via Disc product is for homologous use as an intervertebral disc filler, in a single patient and to only be handled by a licensed healthcare professional.

During the processing of the final product, minimal manipulation is used to ensure the basic function(s) of the composition will not be compromised. The product is made up of two components: viable cells and nucleus pulposus microparticulate.

The cell process incorporates a series of isolation steps to select a cell population that includes Marrow-Isolated Adult Multilineage-Inducible (MIAMI) cells, see US 2015/0132266. The isolation process includes the use of Heparin, DNAse, and Ficoll reagents. The isolated cells are then resuspended in a 100% polyampholyte-based cryoprotectant, aseptically packaged in a tear pouch within a peel pouch configuration and subsequently frozen.

The nucleus pulposus is extracted from recovered intervertebral discs and exposed to a sterile water wash. The nucleus pulposus then undergoes a gentle vacuum cycle to obtain a tissue that is dehydrated. The dehydrated tissue is then ground and filtered to capture the particles that are less than 300 µm in size. The micronized nucleus pulposus tissue is then aseptically packaged in a tear pouch within a peel pouch configuration. Both components of the final product are to be stored at −65° C. or colder.

Figure 16:
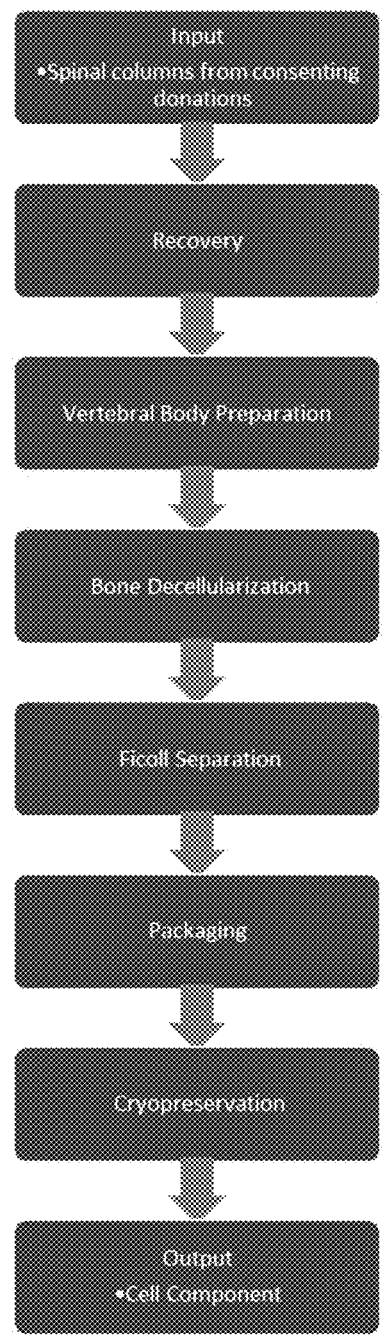
FIG. 16 is a chart showing the cell component subprocess flow.
Figure 17:
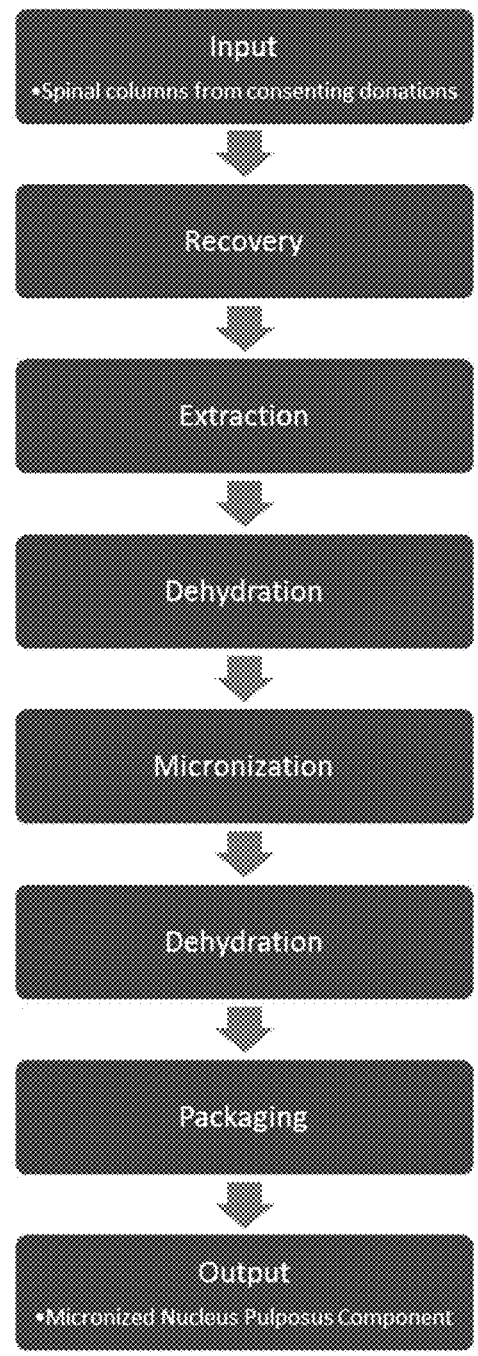
FIG. 17 is a chart showing the micronized nucleus pulposus component subprocess flow.

The process is divided into two subprocesses with their own respective inputs and outputs, as shown in FIGS. 16 and 17.

All manufacturing, including recovery and further processing of the spinal column, is performed using aseptic technique The final packaging configuration for the cell component as well as the micronized nucleus pulposus component consist of a tear pouch within a peel pouch configuration. The outer packaging used for the cell component is a chevron type pouch that allows the end user to easily present the sterile inner pouch containing the product component to a sterile field.

Figure 18:
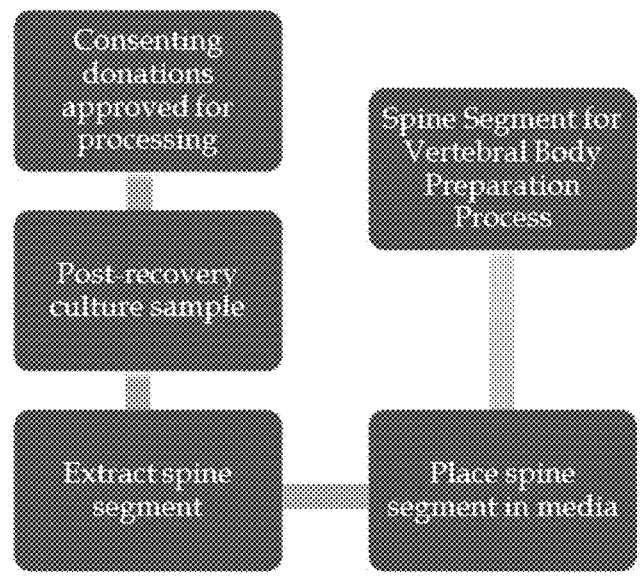
FIG. 18 is a chart showing cell component recovery process.

Cell Component Process includes a Recovery Process as shown in the chart of FIG. 18.

The process is intended to isolate a segment of the spinal column from the consenting donation. The spinal column is accessed posteriorly and transected through the intervertebral disc space(s) to excise the segment. The separated spine segment is then placed into Dulbecco's Modified Eagle Media (DMEM) supplemented with heparin and gentamicin.

Figure 19:
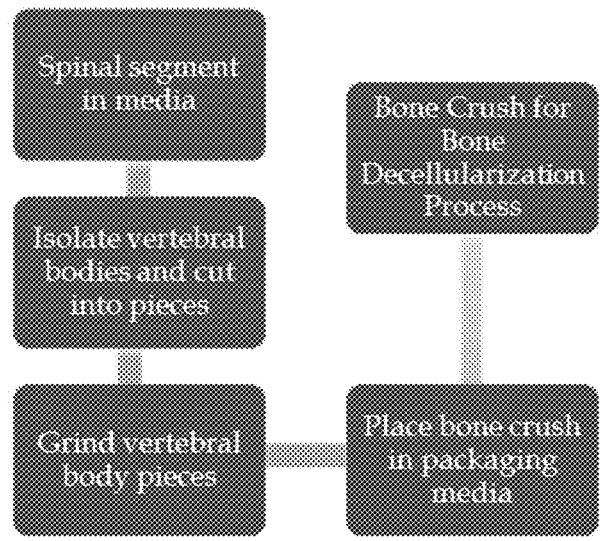
FIG. 19 is a chart showing the vertebral body preparation process.

Cell Component Process further includes the Vertebral Body Preparation Process, illustrated in the chart of FIG. 19.

The vertebral body preparation process is intended to prepare the separated spine segment for the decellularization process. The spine segment is cut in such a way that only the vertebral bodies of each segment is retained. They're immediately placed into packaging media; which is made up of the constituents listed, DMEM, Heparin, Gentamicin, DNAse.

The vertebral bodies are then cut into approximately 1 cm3 pieces with a band saw, excluding any cortical sections, and immediately re-immersed into packaging media. The vertebral body pieces are then ground into 4-10 mm pieces using a bone grinder and are stored in packaging media at 1-10° C. before the decellularization process.

Figure 20:
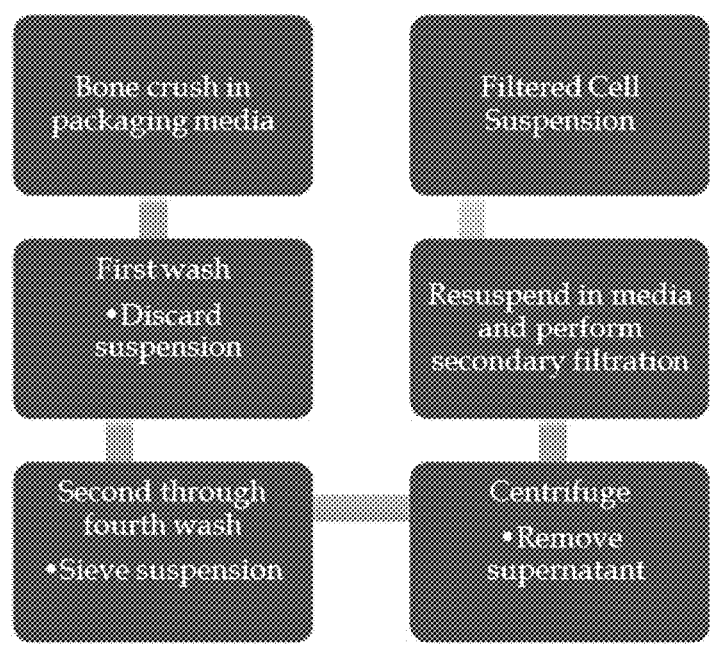
FIG. 20 is a chart showing the bone decellularization process.

Cell Component Process also includes Bone Decellularization Process as shown in FIG. 20.

The cell isolation process is intended to isolate a cell population derived from the mononuclear cell fraction. The bone crush from the vertebral bodies is decellularized using gentle mechanical agitation to shake the cells into suspension.

The first wash is performed on the bone crush using the original media from the vertebral body preparation in a plastic tumbling jar. The jar containing the tissue is then subjected to a tumbling cycle. Upon completion of the tumbling cycle, the mixture is filtered through a stainless steel sieve and the resulting suspension is then discarded.

Three additional washes are performed on the bone chips remaining on the sieves from the tumbling process using processing media as described above. The processing media used for suspending the cells is made up of the constituents listed DMEM—Dulbecco's Modified Eagle Media, Human Serum Albumin, Heparin, Gentamicin, DNAse.

Each constituent of the processing media plays a unique role. Human serum albumin is used to maintain the proper osmotic pressure in the solution containing the cells during processing. Heparin is used to prevent coagulation during processing. Gentamicin is an antibiotic that is used as a preventative measure. DNAse is used in the processing media to catalyze the breakdown of extracellular DNA particles.

Upon completion of each tumbling cycle, the mixture is filtered through stainless steel sieves to separate the bone chips from the cell stock. The filtrate resulting from the washes are spun in the centrifuge and the supernatant is then removed. The cell pellet is resuspended in processing media and further filtered through a blood filter.

Figure 21:
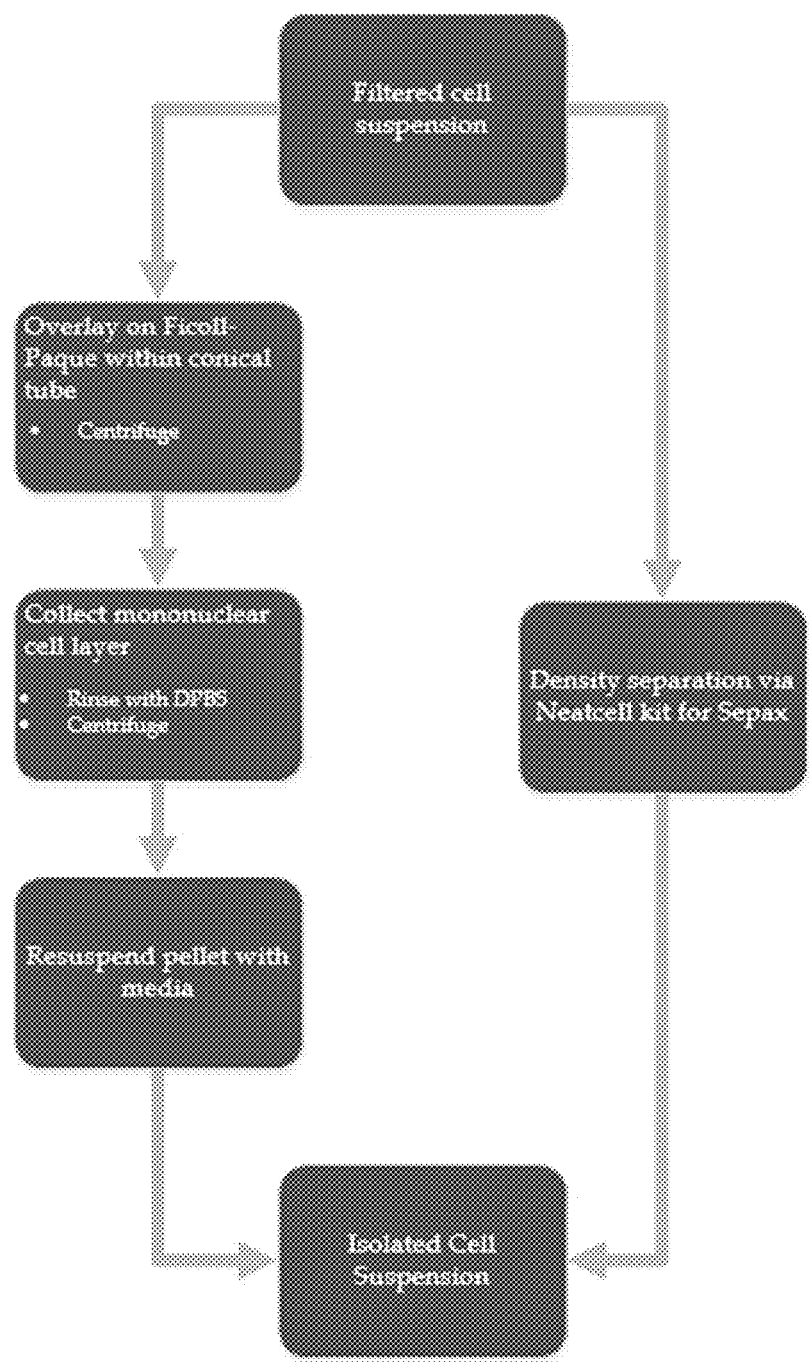
FIG. 21 is a chart showing the Ficoll separation process.

Cell Component Process includes the Ficoll Separation Process illustrated in the chart outline of FIG. 21.

The cell suspension undergoes separation by density to isolate mononuclear cells. The cell suspension is laid over Ficoll-Paque™ and spun in the centrifuge. Centrifugation results in the formation of layers in the conical tubes that include: plasma and other constituents, mononuclear cells, and red blood cells. The desired mononuclear cell layer is collected, the supernatant is removed, and the cell layer is resuspended with DPBS. The diluted cell suspension is then spun in the centrifuge and the resulting pellet is resuspended with DPBS to remove traces of Ficoll-Paque™ and any undesired acellular components. Following the washes with DPBS the cell suspension goes through a centrifugation cycle and the cell pellet is resuspended in processing media without antibiotics.

Density separation and its subsequent washes may alternatively be performed through the use of the Neatcell protocol on Biosafe's Sepax 2 RM automated cell processing system. The Sepax 2 is an instrument that isolates the cells in a closed environment by means of a sterile, single-use, processing kit that consist of a centrifugation chamber, bags, filters, stopcocks and lines to dispense the necessary reagents and collect the final cell suspension. The mechanisms of the computer-controlled device performs the separation with a centrifugal and axial displacement drive to the chamber on the kit, combined with directional valves and sensors.

Figure 22:
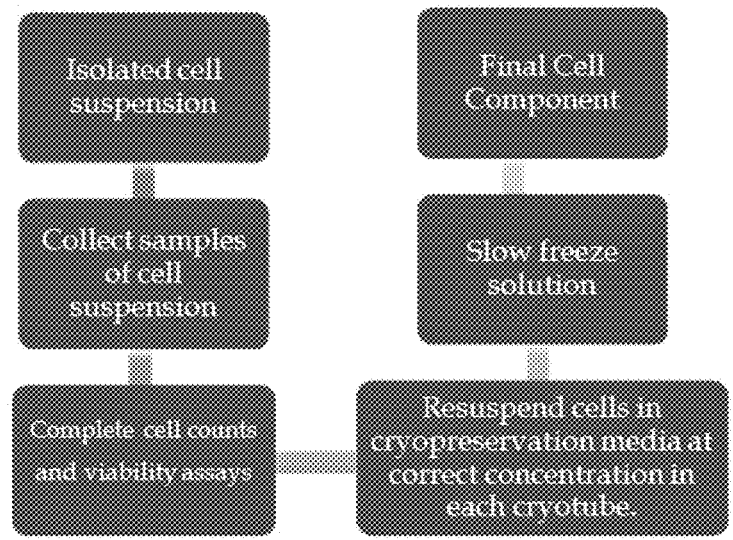
FIG. 22 is a chart showing the packaging and cryopreservation process.

Once this is complete, the Cell Component Process is moved to Packaging and Cryopreservation Process as shown in FIG. 22

Cell counts and viability assays are performed on samples from the final cell suspension through manual methods or using an automated cell counter. Using the cell counts and following centrifugation the cell pellet resuspended in cryopreservation media and aliquoted into cryotubes so as to achieve a concentration of 8.5×106 cells/ml. The cryotubes are then packaged in the final packaging configuration. After the packaging is complete components are placed in a container to achieve a slow freezing rate in a −80° C. freezer. The cells are stored at a temperature of −65° C. or colder through the distribution process to preserve the viability of the cells.

The other main component of the final product is the Micronized Nucleus Pulposus Component and its process is explained in the final charts 23-27.

Figure 23:
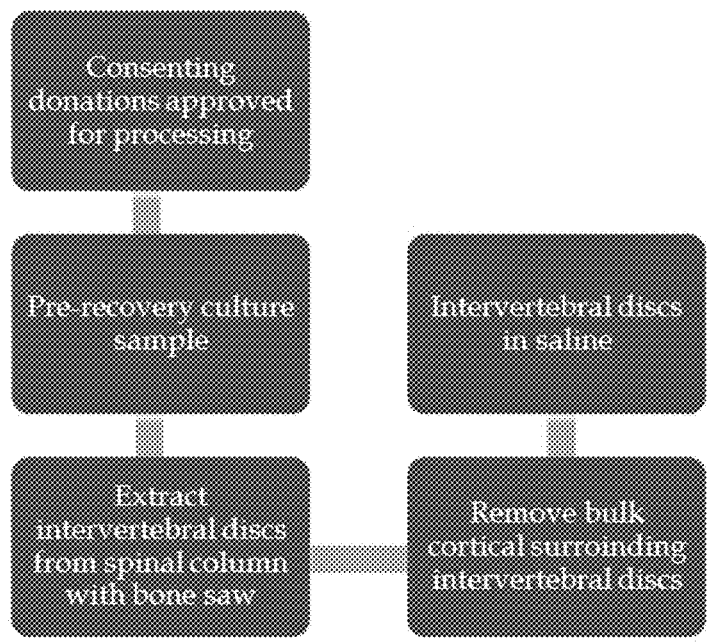
FIG. 23 is a chart showing the micronized nucleus pulposus component recovery process.

Micronized Nucleus Pulposus Component Recovery Process is shown in FIG. 23.

The process is intended to isolate the intervertebral discs of the spine segment from consenting donations. The spine segment is removed of soft tissue residue using a scalpel and each intervertebral disc is excised using a band saw. The intervertebral discs are then placed in saline and frozen at −80° C. until they are processed.

Figure 24:
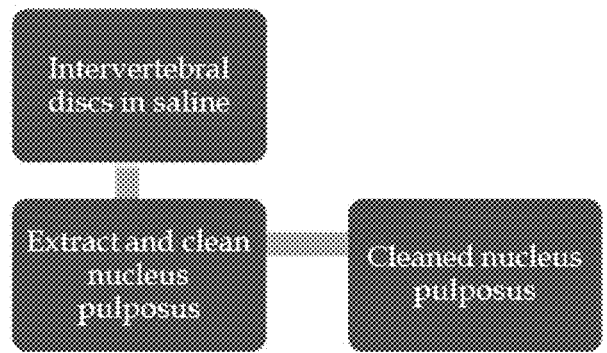
FIG. 24 is a chart showing the micronized nucleus pulposus component extraction process.

Micronized Nucleus Pulposus Component includes an Extraction Process shown in FIG. 24.

The nucleus pulposus is removed from the recovered intervertebral discs. Following removal it is exposed to sterile water to remove residual blood and other unwanted debris. Acceptable cleaned nucleus pulposus must be white or slightly tan and exhibit normal nucleus pulposus tissue integrity. The process of cleaning the nucleus pulposus is minimally manipulative to ensure that the basic function(s) of the natural tissue is retained.

Figure 25:
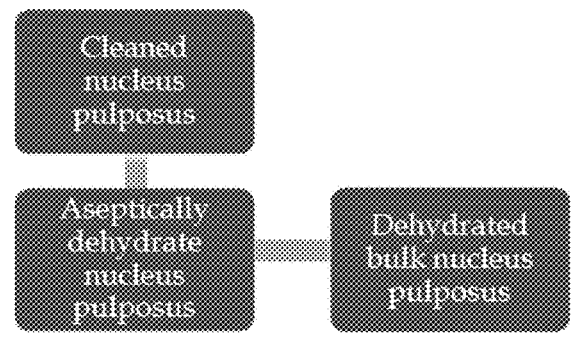
FIG. 25 is a chart showing the micronized nucleus pulposus component dehydration process.

Micronized Nucleus Pulposus Component further includes a Dehydration Process shown in FIG. 25.

Once the extracted nucleus pulposus segments are removed and meet the aforementioned acceptable criteria, they are then prepared to undergo the vacuum drying process. The cleaned nucleus pulposus segments are dehydrated aseptically. The cycle used has shown to sufficiently dehydrate the tissue without affecting the basic function(s) of the tissue.

Figure 26:
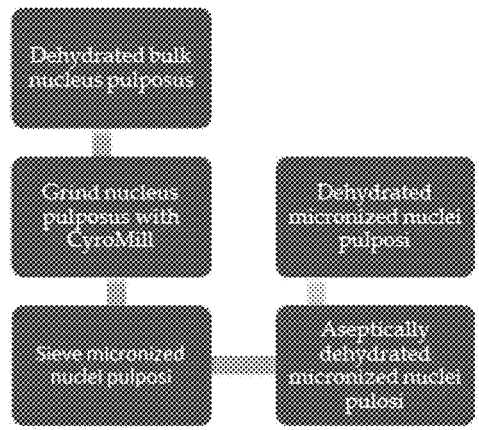
FIG. 26 is a chart showing the micronized nucleus pulposus component micronization and dehydration process.

Micronized Nucleus Pulposus Component includes Micronization and Dehydration Process are as outlined in FIG. 26.

Once the nucleus pulposus has been thoroughly dehydrated, it is subjected to a micronization process. The nucleus pulposus is cut into segments, ground and the target microparticulate size is selected through the use of sieves. The microparticulate is then dehydrated aseptically.

Figure 27:
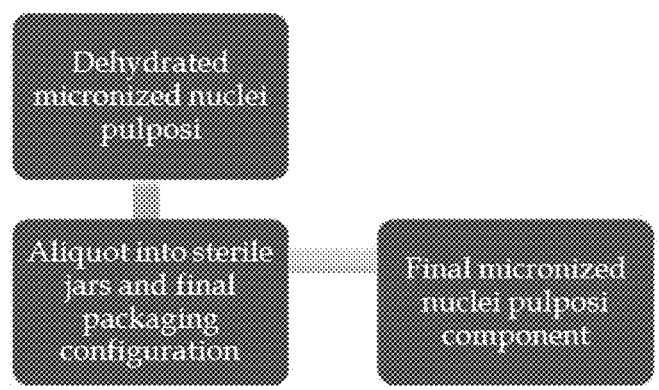
FIG. 27 is a chart showing the micronized nucleus pulposus component packaging process.

Micronized Nucleus Pulposus Component has a final Packaging Process shown in FIG. 27.

The dehydrated micronized nuclei pulposi is packaged in sterile jars with inner liners and screw top lids in the final product size 0.75 cc. The jars are then packaged in the final configuration.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A cryopreserved composition comprising:
   i) a nucleus pulposus, wherein the nucleus pulposus is human-derived, dehydrated, and micronized;
   ii) a bone-marrow-derived mixture of components including non-whole cellular components, the non-whole cellular components including vesicular components, active and inactive components of biological activity, cell fragments, cellular excretions, cellular derivatives, and extracellular components;
   iii) a biologically compatible, polyampholyte, protectant or cryoprotectant; and
   iv) optionally, saline.

2. The composition of claim 1, wherein the composition further includes non-expanded, bone marrow-derived, whole cells.

3. The composition of claim 2, wherein the non-expanded, bone marrow-derived, whole cells are being pluripotent stem cells.

4. The composition of claim 2, wherein the non-expanded, bone marrow-derived, whole cells are non-differentiated, non-committed cells.

5. The composition of claim 1, wherein the protectant or cryoprotectant creates a physical or electrical or chemical gradient or combination thereof for tissue regeneration.

6. The composition of claim 1, further includes organelle fragments.

7. The composition of claim 1, wherein the nucleus pulposus has particles sized less than 400 microns.

8. The composition of claim 7, wherein the nucleus pulposus is a powder.

9. The composition of claim 1, wherein the composition when rehydrated has a viscosity such that the composition is flowable through a 2-4 mm cannula.

10. The composition of claim 9 wherein the composition is contained in a syringe or other injectable device.

11. A kit comprising:
    i) a quantity nucleus pulposus, wherein the nucleus pulposus is human-derived, dehydrated, and micronized; and
    ii) a mixture comprising,
    a) a bone-marrow-derived mixture of components including non-whole cellular components, the non-whole cellular components including vesicular components, active and inactive components of biological activity, cell fragments, cellular excretions, cellular derivatives, and extracellular components;
    b) a biologically compatible polyampholyte protectant or cryoprotectant; and
    iii) optionally, saline.

* * * * *